(12) United States Patent
Potts

(10) Patent No.: US 8,304,208 B2
(45) Date of Patent: Nov. 6, 2012

(54) ASSAYS FOR PERFORMANCE OF ORGANISMS IN PHENOTRONS

(75) Inventor: Wayne K. Potts, Salt Lake City, UT (US)

(73) Assignee: The University of Utah Research Foundation, Salt Lake City, UT (US)

(*) Notice: Subject to any disclaimer, the term of this patent is extended or adjusted under 35 U.S.C. 154(b) by 0 days.

(21) Appl. No.: 12/994,394

(22) PCT Filed: May 28, 2009

(86) PCT No.: PCT/US2009/045517
§ 371 (c)(1),
(2), (4) Date: Jun. 6, 2011

(87) PCT Pub. No.: WO2009/148927
PCT Pub. Date: Dec. 10, 2009

(65) Prior Publication Data
US 2011/0229925 A1    Sep. 22, 2011

Related U.S. Application Data

(60) Provisional application No. 61/130,199, filed on May 29, 2008.

(51) Int. Cl.
*C12Q 1/02* (2006.01)
*C12M 1/34* (2006.01)
*G01N 33/48* (2006.01)
*G06F 19/00* (2011.01)

(52) U.S. Cl. ......... 435/29; 73/865.8; 435/287.1; 702/19

(58) Field of Classification Search ................... 435/29, 435/287.1; 73/865.8; 702/19
See application file for complete search history.

(56) References Cited

U.S. PATENT DOCUMENTS

2005/0136434 A1   6/2005   Xu et al.
2005/0153378 A1   7/2005   Takagi et al.

OTHER PUBLICATIONS

International Search Report and Written Opinion from PCT/2009/045517, dated Jan. 29, 2010.

Ely D L et al., "A Monitoring Technique Providing Quantitative Rodent Behavior Analysis", Physiology and Behavior, Elsevier Science Ltd., Oxfor, GB, vol. 9, No. 4, Oct. 1, 1972, pp. 675-679.
Ely D et al., "Minicomputer Monitored Social Behavior of Mice with Hippocampus Lesions", Behavioral Biology Jan. 1976 LNKD-PUBMED: 943156, vol. 16, No. 1, Jan. 1976, pp. 1-29.
Weidt et al., "Not Only Mate Choice Matters: Fitness Consequences of Social Partner Choice in Female House Mice", Animal Behaviour, Bailliere Tindal, London, GB, vol. 75, No. 3, Oct. 23, 2007, pp. 801-808.
Oliviero C et al., "Using Movement Sensors to Detect the Onset of Farrowing" Biosystems Engineering, Academic Press, UK, vol. 100, No. 2, Jun. 1, 2008, pp. 281-285.
Ragnauth A K et al., "Female Oxytocin Gene-Knockout Mice, in a Semi-Natural Environment, Display Exaggerated Aggressive Behavior.", Genes, Brain, and Behavior, Jun. 2005 LNKD-PUBMED: 15924555, vol. 4, No. 4, Jun. 2005, pp. 229-239.
Ilmonen Petteri et al., "Major Histocompatibility Complex Heterozygosity Reduces Fitness in Experimentally Infected Mice." Genetics Aug. 2007 LNKD-PUBMED: 17603099, pp. 2501-2508.
Carroll Lara S et al., "Fitness Effects of a Selfish Gene (the *Mus t* Complex) are Revealed in an Ecological Context." Evolution; International Journal of Organic Evolution Jun. 2004 LNKD-PUBMED: 15266980, vol. 58, No. 6, Jun. 2004, pp. 1318-1328.
Meagher S et al., "Male-Male Competition Magnifies Inbreeding Depression in Wild House Mice." Proceedings of the National Academy of Sciences of the United States of America Mar. 28, 2000, vol. 97, No. 7, pp. 3324-3329.

*Primary Examiner* — Herbert J Lilling
(74) *Attorney, Agent, or Firm* — Workman Nydegger

(57) ABSTRACT

A phenotron assay can be used for determining an adverse effect on health by: identifying an exposure condition to be studied for an adverse effect on the health of an organism; providing a phenotron having one or more sensors each configured to sense a signal; introducing one or more test founder organisms into the phenotron, said test founder organisms each having a signal emitting tag that is sensed by the one or more sensors and each being exposed to the exposure condition; introducing one or more control founder organisms into the phenotron, said control founder organisms each having a signal emitting tag that is sensed by the one or more sensors and none of said control founder organisms being exposed to the exposure condition; collecting, from the one or more sensors, signals from the tags to obtain data indicative of a parameter of the health of the one or more test founder organisms compared to the one or more control founder organisms; and determining from the data whether the exposure condition has an adverse effect on the health of the one or more test founder organisms.

49 Claims, 5 Drawing Sheets

ASSAYS FOR PERFORMANCE OF ORGANISMS IN PHENOTRONS

CROSS-REFERENCE TO RELATED APPLICATIONS

This patent application claims benefit of U.S. Provisional Patent Application Ser. No. 61/130,199, filed May 29, 2008, which is incorporated herein by specific reference in its entirety.

BACKGROUND OF THE INVENTION

In our current environment and lifestyles, many substances or conditions once considered safe are found to be sources of adverse health and illness. For example, humans are often exposed to various chemicals, pharmaceuticals, vaccines, therapeutic agents, pathogens, electromagnetic radiation, excess or deficiencies of nutrients, food additives, food supplements, electromagnetic radiation, and numerous other exogenous insults that may have unforeseen and adverse effects on our health. Often, these substances or conditions are determined to be sufficiently benign at a particular level due to inadequacies in testing; however, the level is later determined to impart adverse effects on health. It may take years or decades of epidemiological or experimental research in order to determine that a substance or condition once considered safe may actually be related to or a source of adverse health and illness. As a result, humanity often becomes the test subject for many substances or conditions that are used in various consumer goods, foods, plastics, and manufacturing practices.

To prevent such uncontrolled experimentation on unsuspecting human subjects, there is a great need for broad, sensitive assays that are able to detect the adverse health consequences of any agent or condition in a living model. While science has provided many types of assays that can be conducted to determine the effects of substances or exposures at cellular and molecular levels, a biological target and detectable effect of the substance must be known. Without any prior knowledge that a substance or exposure is affecting a certain biological pathway, such organ- or pathway-specific assays as general screens for toxic affects.

Thus, it would be advantageous to have an assay that can identify overall health status of an organism in response to a particular substance or combination of substances or exposure to certain conditions. It would also be beneficial to be able to determine a particular aspect of health that is impacted so that further studies of the biological pathways can be devised and conducted.

BRIEF SUMMARY OF THE INVENTION

In one embodiment, the present invention is related to a phenotron assay. A phenotron is a sensitive phenotyping instrument that uses the stresses of seminatural conditions to reveal treatment-caused health (performance) declines of treatment and control animals in direct competition with each other. The phenotron assay can be used for determining an adverse effect on health by the following: identifying an exposure condition to be studied for an adverse effect on the health of an organism; providing a phenotron having one or more sensors each configured to sense a signal; introducing one or more test founder organisms into the phenotron, said test founder organisms each having a signal emitting tag that is sensed by the one or more sensors and each being exposed to the exposure condition; introducing one or more control founder organisms into the phenotron, said control founder organisms each having a signal emitting tag that is sensed by the one or more sensors and none of said control founder organisms being exposed to the exposure condition; collecting, from the one or more sensors, signals from the tags to obtain data indicative of a parameter of the health of the one or more test founder organisms compared to the one or more control founder organisms; and determining from the data whether the exposure condition has an adverse effect on the health of the one or more test founder organisms.

Another phenotron assay can include: identifying an exposure condition to be studied for an adverse effect on the health of an organism; introducing one or more test founder organisms into the phenotron, said test founder organisms each being exposed to the exposure condition; introducing one or more control founder organisms into the phenotron, none of said control founder organisms being exposed to the exposure condition; collecting data from the founder organisms in the phenotron indicative of a parameter of the health of the one or more test founder organisms compared to the one or more control founder organisms; determining from the data whether the exposure condition has an adverse effect on the health of the one or more test founder organisms; and inputting the data into a computing system.

In one embodiment, the present invention can include a phenotron system having one or more of the following: an enclosure configured to retain one or more organisms of the same type; one or more distinct regions of the enclosure; one or more feeders within each region; one or more nesting areas within each region; and one or more sensors configured to be operably associated with each one or more feeders and/or one or more nesting areas. Optionally, the phenotron system can include: one or more transmitting devices configured to be operably associated with the one or more sensors; a computing system configured for communicating with the one or more transmitting devices to receive data from the one or more sensors; a receiver configured to be operably coupled with the computing system so as to be capable of communicating with the one or more transmitting devices; or one or more tags configured to be associated with one or more organisms and for communicating with the one or more sensors, wherein the one or more tags can be configured for communicating data to the one or more sensors.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
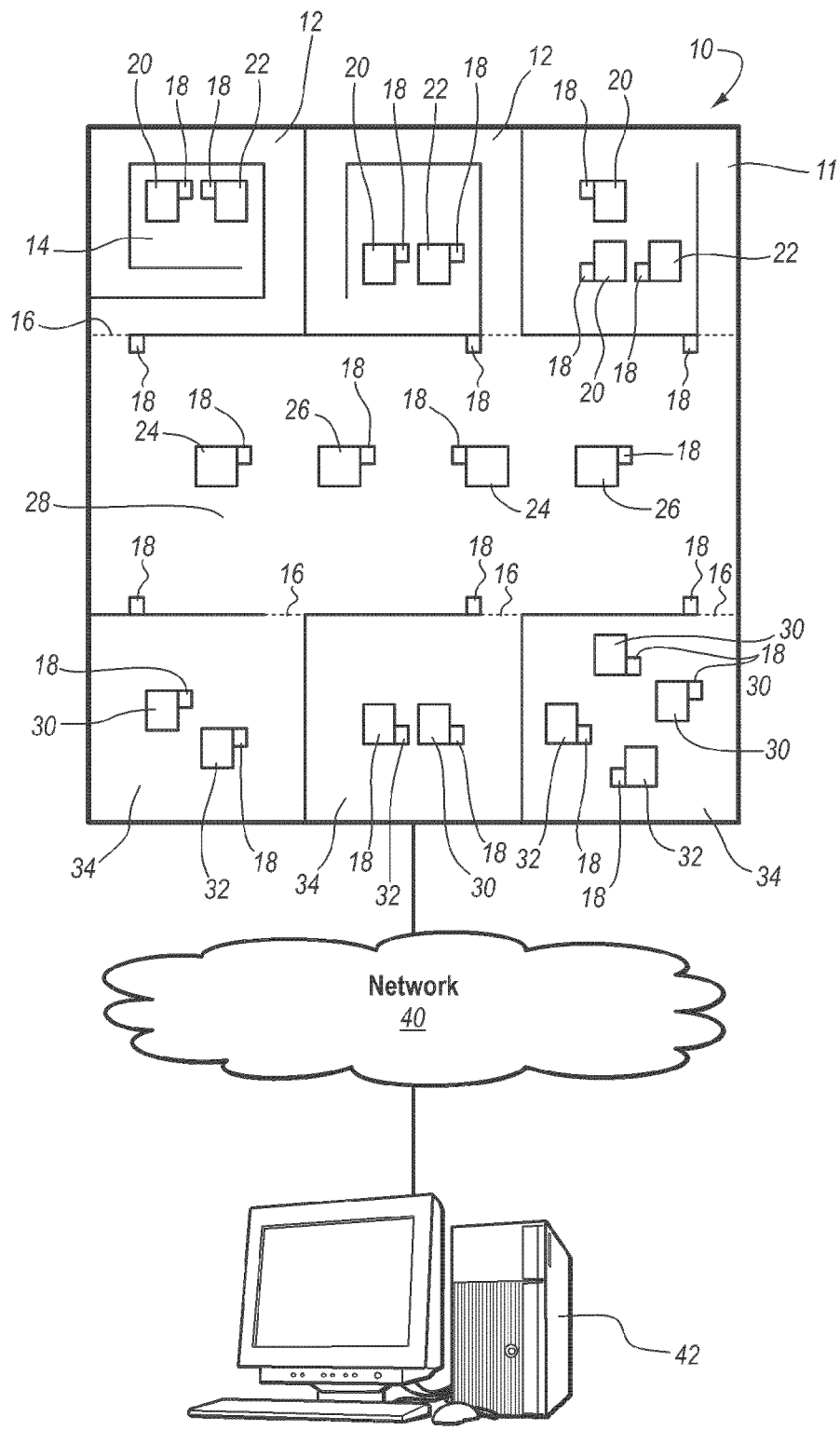
FIG. 1 illustrates an exemplary phenotron.

Generally, the present invention is related to a novel phenotron system and methods of use for studying broad and specific health consequences in organism in response to various exposure conditions, such as to substances, radiation, or the like. The phenotron system is configured to provide data that can be used in determining whether an exposure condition may be harmful to humans. Additionally, detailed studies can now be performed to determine health consequences even in the absence of a known biological target of the exposure condition, because high performance from most physiological and behavioral systems is required for individual success in seminatural populations, measured by survival, social dominance, reproduction and a variety of other fitness components. Consequently, any suspected toxin that decreases performance of any physiological system is likely to be detected.

Previous phenotron systems are explained in: Mating patterns in seminatural populations of mice influenced by MHC genotype; W K Potts C J Manning, and E K Wakeland; Nature; vol. 352; pp. 619-621 (Aug. 15, 1991); Communal nesting patterns in mice implicate MHC genes in kin recognition; C J Manning, E K Wakeland, and W K Potts; Nature; vol. 360; pp 581-583 (Dec. 10, 1992); Experimental infection magnifies inbreeding depression in house mice; P Ilmonen et al.; J. Evol. Biol.; vol. 21; pp. 834-841 (2008); Male-male competition magnifies inbreeding depression in wild house mice; S Meagher, D J Penn, and W K Potts; PNAS; Vol. 97; No. 7; pp. 3324-3329 (Mar. 28, 2000); Fitness effects of a selfish gene (The Mus T complex) are revealed in an ecological context; L S Carroll et al.; Evolution; Vol. 58. No. 6; pp. 1318-1428 (2004); and L S Carroll and W K Potts; Advances In The Study Of Behavior; Vol. 36; pp. 173-215 (2006).

It has been found that many toxic substances exert their adverse effects in ways that are difficult to detect. As such, detailed experimental studies in model systems or detailed observational studies in humans such as long-term epidemiological studies resulted in determining that substances or conditions once believed to be benign were actually harmful. In particular, the establishment of low dose effects have often required years and even decades of such detailed studies on substances such as Teflon, PCBs, second-hand smoke, DDT, asbestos and lead. There are likely to be even more toxins or conditions that have adverse consequences on health that have never been discovered because the physiological impairments produce symptoms too diffuse or subtle to raise concerns or warrant large scale epidemiological studies. When the biological network or specific biological pathway that is compromised by an exposure condition (e.g., substance or condition) is unknown, then screening or detecting the adverse health consequences is extremely challenging and akin to the needle-in-the-haystack problem.

The phenotron assay methods can be used to compare how test organisms compete against sham-treated organisms (e.g., controls). The phenotron can receive test organisms and control organisms so that there is direct competition for survival, where such a test configuration can be referred to as a seminatural environment because it mimics a natural competitive environment even though the competition is within an enclosure. Such competitive environments require the organisms to have and maintain a high performance level from all or nearly all physiological systems. Thus, the phenotron and associated assay methods provide for conditions that are sensitive to otherwise subtle alterations in individual physiological systems and changes due to exposure conditions.

Accordingly, the phenotron assay methods can be used to determine whether an exposure condition reduces performance (health) of various physiological systems in the experimental organisms compared to sham-treated controls. The phenotron assay is both broad and sensitive because high performance from many, important, or all physiological systems may be needed for individual success. The success of an individual organism in the phenotron can be determined by survival, social dominance, reproduction, and a variety of other components of fitness and health.

The phenotrons can be useful in organism performance assays, which can simultaneously provide broad and sensitive screens for selected exposure conditions. While many applications can utilize substances, natural or unnatural environmental conditions can also be studied for adverse health consequences in the phenotrons. Any potentially toxic substance or condition that reduces performance of any physiological system can be studied with the phenotron assay, even when the health consequences are difficult to identify. For example, the phenotron assay can study various substances that are pervasive in the environment that may possess qualities that make absolute toxicity difficult to assess using classical or molecular measures. The exposure conditions can be tested near the lowest dose of observed effect, and substantial fitness declines can be identified and/or predicted. Additionally, the increased ability to detect adverse health consequences using this experimental system can contribute to the discovery and characterization of molecular, cellular, and physiological mechanisms underlying the toxicity. The aspect of health that is adversely impacted can then be thoroughly studied using traditional approaches in biotechnology so that one or more biological targets that are effected by the exposure condition can be identified. Thus, biological targets for therapeutics may be identified that heretofore would be unidentifiable.

As shown in the examples, the phenotron assay can be more sensitive (e.g., 50 times more sensitive) than previous methods in detecting the adverse consequences of inbreeding, revealing substantial fitness declines at inbreeding levels previously considered benign. The phenotron-proven adverse effects of low-level inbreeding can be used as an example and basis for using the phenotron assays to study the health consequences of low-dose toxin exposure. The phenotron has been used to detect (e.g., with great sensitivity) differential physiological performance caused both by genetic treatments (described below), and by the potential toxin tested (e.g., high fructose corn syrup). The phenotrons in these experiments showed major fitness consequences when experimental mice competed directly against controls in seminatural populations; however, detectable phenotypes were largely invisible to conventional methods. Once identified, phenotypic defects due to mutations or toxins can be studied for their molecular and cellular basis.

In one embodiment, the phenotron assay can be used to study various physiological systems simultaneously under conditions that require generalized high organism performance. The assay can take advantage of the stressful and competitive conditions found in organisms (e.g., house mice) living in seminatural conditions, for which competitive success requires high performance from most physiological systems. Success and failure can be measured because all the competitors are aimed at the same goal: survival and high reproductive success. Also, the phenotron allows for an analysis of many different components of fitness that important for survival and high reproductive success.

The phenotron assay can provide information that was previously difficult to obtain. For example, a 10% reduction in metabolic efficiency may have no detectable effect on mouse health, longevity, or reproduction in a benign, laboratory environment. However, the same reduction may be effectively lethal under the stressful and competitive conditions found in nature. Since physiological systems in organisms evolved to solve problems found in nature, the phenotron is designed to use these natural problems to evaluate potential toxins for adverse effects. The same 10% metabolic defect may go unnoticed in humans using current medical practices, but if the sufferer could suddenly eliminate the defect, an increase in their quality of life may be recognizable and desirable, particularly if they participated in athletic endeavors. In nature, mice live an athletic lifestyle, especially during escalated wrestling matches over territories, and if a treatment affects their performance, it is sensitively revealed through failures to win contests over resources, reproductive output, survival and a host of other components of fitness. Besides mice, this theory is applicable to substantially all organisms, because it is the rare organism that never has to compete for resources.

In one embodiment, the organism to study in the phenotron is a house mouse because it is an ideal organism for such an approach. First, it is a mammal and has physiological properties similar to humans and other domesticated animals. Second, it is the best studied mammalian model organism, and thus comes with the best molecular and physiological understanding of its biological networks, pathways, and components. Third, the high level of competition present in mouse societies demands high performance from most physiological systems, which allows the detection of adverse effects from suspected toxins or other experimental variables. Fourth, there has been remarkable success at detecting health and performance declines due to genetic variables and one potential toxin that had been completely missed or whose adverse effects had been grossly underestimated by more conventional lab-based assays. Finally, it is by far the most cost effective mammal to maintain and with which to conduct the necessary phenotron-based experiments.

The phenotrons are configured for use with seminatural populations of organisms (e.g., house mice). FIG. 1 is an illustration of a phenotron 10 for use with mice; however, phenotrons can be created for any organism based on the living parameters of the organism and captivity requirements.

FIG. 1 shows an enclosure 11 divided by walls into one or more distinct regions 12 of the enclosure. One is configured an optimal region 14 because it is more enclosed. Each region 12 is shown to have a feeder 20 associated with a sensor 18 (e.g. RFID or video camera). The optimal region 14 is accessible by a controlled gate 16 that is associated with a sensor 18. Each region 12 also includes a nesting area 22 associated with a sensor 18. On open region 28 is shown to be less enclosed and is likely to be less favorable to dominant and successful males. This open region 28 includes open feeders 24 associated with sensors 18, and open nesting boxes 26 associated with sensors 18.

The phenotron 10 also shows some medium favorable areas 34, each including a medium feeder 30 associated with a sensor 18, and a medium nest box 32 associated with a sensor. The medium favorable areas 34 are shown to include gates 16 operable by sensors.

The sensors are configured to receive information from tags (not shown) associated with the organisms. The sensors can be passive and read information regarding the tags in proximity, or the sensors can control access to areas, food, or nests. The feeders are considered to be food and/or water sources. Any particular feeder can be configured to give only test food to test organisms and control food to control organisms. Alternatively, there may be additional gates that selectively control access to an area with a feeder that only allows test organisms to feed from test feeders, and control organisms to feed from control feeders. Many different permutations of phenotrons using the features described herein can be configured or created from the teachings hereon.

As shown in FIG. 1, the sensors 18 are also transmitting devices. These sensors can communicate through a network 40 (e.g., wireless or wired) in order to provide sensor and tag data for the test and control organisms to the computing system 42. For example, the computing system 42 can be a standard computer. Also, more complex sensors 18 can transmit biometrics through the network 42 to the computing system 42. Also, the computing system 42 can transmit data or instructions to the sensors 42 through the network to control the gates 16, feeders 20, and/or nest boxes 22.

The phenotron for mice can vary in sizes ranging from 25 to 50 $m^2$, but could be smaller for single male phenotrons and larger for phenotrons having a large number of males. The phenotrons can be configured such that the test population can be exposed to any treatment, substance or condition. The relative success of control and experimental mice can be compared for any measurable components of fitness allowing detection of any reduced performance due to treatment.

The phenotron can be used for revealing toxicity phenotypes as a first step in the process of determining the mechanism of the adverse health consequence. Without first understanding that an exposure has adverse health consequences, there may not be a viable reason for researching and determining the mechanistic basis of toxicity. Identification of adverse health and the aspects of health that are compromised can be used to identify the biological networks, pathways, and components that can then be tested for being a biological target. After biological targets are identified, the molecular basis of these adverse health consequences can be studied under traditional approaches.

In one embodiment, the phenotron can be used to study toxins. Examples of toxins can include lead, cadmium, arsenic, bisphenol A, and atrazine, or others. As such, the phenotron can be used to study toxins with qualities that make absolute toxicity difficult to assess using classical or molecular measures. This is particularly true when attempting to determine safe doses of known toxins. For each toxin, one to six or more independent phenotrons having seminatural populations can be prepared where 50% of the phenotron founders (e.g., organisms introduced into the phenotron to initiate the experiment) have been exposed to the specific toxin (e.g., throughout conception, gestation and/or development to adulthood; the other 50% of founders can be sham-exposed or unexposed controls. All phenotron populations can proceed without intervention for a desired period of time. For example, the study can be conducted for 8 months, which represents approximately ½ to ¾ of the house mouse life span.

During the phenotron assay, detailed behavioral and population data can be collected by various methods of data collection. The data can be used to determine the specific components of fitness that are effected, which can be related to overall health or specific aspects of health. In one option, the data can be collected by visual analysis, and then recorded into a computing system for analysis and graphical generation. Also, the data can be collected in the phenotron via sensors that sense the activities and interactions of individuals in the population. The sensors can be configured to distinguish between test and control subjects. For example, the individual founders in the phenotron can have some device that can allow the sensor to receive the data. Examples can be transmitters, transceivers, RFID, or the like.

In one example, using individual-specific passive integrated transceiver (PIT) tags implanted in or attached to each of the founders and optionally with behavioral observations, a determination of health can be obtained. The tags and/or observations can be used to monitor social status, outcomes of aggressive encounters, territory boundaries, female settlement patterns, pregnancies, litter sizes at birth, weaning success, mating encounters and many other behaviors critical to estimating various components of fitness, including age- and sex-specific survival, fertilities, fecundities, and weaning success, or many other parameters. The reproductive fitness of founders can be determined using genetic analysis, such as with microsatellite genetic markers. Identification of the specific components of fitness that are compromised by each toxin can be used to identify the biological networks, pathways, and molecular, cellular and physiological mechanisms affected by the toxin.

The toxin can be administered in a variety of ways, such as in food, water, or through other exposures. In fact, any method of drug administration could be adapted for administration of the toxin, and exposure conditions can be administered in any manner that the exposure can occur, which are exposure-dependent. For example, the toxin can be administered via ad libitum water ingestion continuously or intermittently. The toxic can be administered at any time from fetal development through early adulthood. For fetal development administration, exposure can begin with the male and female parents of experimental animals, one week before breeding cages are established, or after breeding cages are created. The exposure can continue via the cage's water source until the offspring are weaned (e.g., generally 6 weeks from conception to weaning). Weaned offspring can continue to be exposed until they are 3 months of age at which point they can either enter populations or be utilized for other experimental measures. Continuous exposure can be conducted with implants having the toxin or via sensor controlled feeders and/or waterers in the phenotron. Controls will be age matched, sham-treated and undergo identical environmental conditions except for exposure to suspected toxin. Feeders are considered to be or include waterers herein.

Optionally, size, weight, and/or water intake measurements of a subset (e.g., 10) of controls and experimental animals can be taken at defined (e.g., weekly) intervals to determine if the presence of the toxin impacts water intake or weight gain. For some toxins, such as arsenic and lead, blood levels of a subset (e.g., 10 animals) of the test and control founders can be measured at the end of exposure to determine biologically active levels of the toxins, and/or measured at various times after exposure. For other toxins, such as Cd, a subset of test and control founders can have their urine levels analyzed to test for toxin accumulation in the kidney.

Experimental solutions having the toxins can be made from stock chemicals and administered via the food and/or water sources. For the purposes herein, food and feeding can be considered to include water and drinking, and vice versa. The toxins (e.g., sodium arsenite, BPA, $CdCl_2$, $PbCl_2$ and atrazine) can be obtained in high-purity research grade stocks. These stocks can be mixed with DI water to create drinking water solutions at the target doses (see Table 1 for exemplary toxin specific doses). Some toxins, such as atrazine can be prepared as a suspension, emulsion, or other formulation with a carrier (e.g., 1.0% methylcellulose) before being added to food or distilled water.

TABLE 1

| Agent | Experimental dose |
| --- | --- |
| Arsenic | 50 µg/l |
| Atrazine | 18 mg/l |
| Bisphenol A | 3 mg/l |
| Cadmium | 5 mg/l |
| Lead | 100 µg/l |

The number of males and females in the test founders and control founders can be the same or different. For example, the test or control founder population can include 10 females and 5 males. The mice can be from an outbred, wild-caught colony, and randomly picked with the exception that founders are unrelated. For genetic analysis of the progeny, it can be beneficial that the experimental and control animals differ for two sex specific polymorphic markers segregating on the Y-chromosome and mitochondria that allow us to assign unique markers to treatment group. The animals can also be from well characterized laboratory strains.

In one example, the phenotron can include indoor enclosures, such as large cages. This can allow for studies year round, independent of weather. Each phenotron can be sub-divided into a plurality of (e.g., six) subsections that are inter-accessible. The subsections can be defined by cage materials with openings, by hardware cloth, metal, wires, fencing, or any manner that provides spatial complexity. Each subsection can include one or more feeders, water sources, and nest boxes. Each test and control founder can be marked for visual analysis and identification through close-focus binoculars. Behavioral observations and nest checks can be conducted to determine social status, territory boundaries, female settlement patterns, pregnancies, litter sizes at birth and weaning, mating encounters and many other behaviors critical to estimating various components of fitness.

Figure 7:
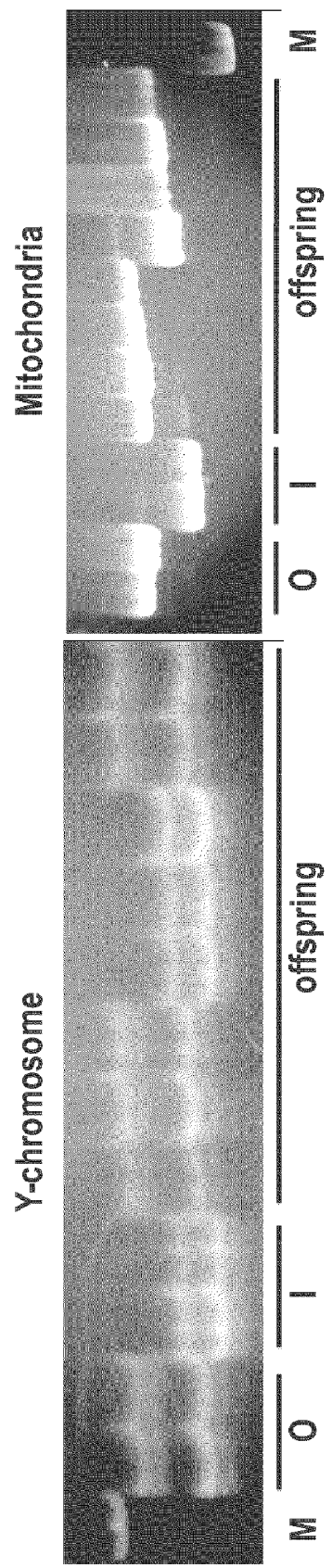
FIG. 7 is a picture of an acrylamide gel illustrating Y-chromosome and mitochondrial genetic markers, and showing that all outbred (O) and (inbred) treatment founders have non-overlapping markers, the reproductive output of each treatment group can be determined with only two genotypings.

In one embodiment, genetic analysis of sex specific markers can allow for efficient and accurate determination of the relative success of experimental and control animals in reproduction. The use of the sex-specific MtDNA and Y markers (FIG. 7) allows data to be obtained about the relative fitness measures of each treatment group because population founders are chosen so that treatment classes have no overlapping alleles. It is theorized that higher reproduction attributed to a test or control founder group can provide an indication that the health is superior due to the aggressive tendencies, territorial behaviors, and mating patterns.

In one embodiment, parentage analysis can be used to provide data regarding the fitness and health of each founder. Parentage can be determined for progeny by amplifying and scoring alleles of a mitochondrial length polymorphism and approximately eleven autosomal and one y-chromosome microsatellite loci. For example, previously these thirteen loci were analyzed for parentage analysis on 1159 progeny from 7 of the 10 t complex populations, and the data were sufficient to parent type 96% of these progeny. The parentage can be assessed by many well-known genetic tools. For example, all primers can be fluorescently tagged with Cy-5 or Cy-3 dye and visualized using a Typhoon fluorimager and ImageQuant software (Molecular Dynamics). Parentage analysis can be facilitated by a computer program using an algorithm designed to systematically construct all possible parental-pup matches through a series of iterative exclusions of founders without matching alleles.

In one embodiment, further assays and analyses can be performed once an adverse health consequence is found that is attributed to the exposure condition. Some of the additional assays and analyses can include: (1) investigate the molecular, cellular and physiological mechanisms causing the health consequence to determine the biological pathway, network, and/or components that are targeted by the exposure condition; (2) use the mechanisms to evaluate whether similar mechanistic effects can occur in humans under similar exposure; (3) determine whether toxins or exposures known to cause long-term problems in humans, such as cancer and heart disease, are forewarned by reduced performance in phenotron assays in mice (e.g., arsenic induced vascular remodeling is associated with both heart disease and tumorigenesis, but significant declines in fitness may occur before the onset of these diseases); (4) test additional toxins to evaluate the range of the phenotron assay; (5) titrate the toxicity in phenotron assays to determine biologically relevant and/or minimal or no observed adverse effect levels (NOAELs); (6) evaluate combinations of suspected toxins, drugs etc. as many substances or conditions can have synergistic interactions (7) develop high throughput phenotron conditions to expedite general screens for potential toxins; or the like.

In one embodiment, the present invention provides a method for determining an adverse effect on health, the steps thereof can be in the order as recited herein or interchanged as needed or desired. The step in the method can include identifying an exposure condition to be studied for an adverse effect on the health of an organism. The exposure condition can be a substance or another condition such as light, radiation, or the like. Another step can include providing a phenotron having one or more sensors each configured to sense a signal. The phenotron and sensors can be configured as described herein. Another step can include introducing one or more test founder organisms into the phenotron. The test founder organisms can each have a signal emitting tag that is sensed by one or more sensors, and each test founder can be exposed to the exposure condition. Another step can include introducing one or more control founder organisms into the phenotron. The control founder organisms can each have a signal emitting tag that is sensed by one or more sensors, and none of the control founder organisms should be exposed to the exposure condition. Another step can include collecting, from the one or more sensors, signals from the tags to obtain data indicative of a parameter of the health of the one or more test founder organisms compared to the one or more control founder organisms. Another step can include determining from the data whether the exposure condition has an adverse effect on the health of the one or more test founder organisms. When adverse health is manifested in the test founders compared to the control founders, there is a strong indication that the exposure condition may be a cause of adverse health.

In one embodiment, a variation of the phenotron assay can include: identifying an exposure condition to be studied for an adverse effect on the health of an organism; introducing one or more test founder organisms into the phenotron, said test founder organisms each being exposed to the exposure condition, but the test founders do not include a tag; introducing one or more control founder organisms into the phenotron, none of said control founder organisms being exposed to the exposure condition, but the control founders do not include a tag; collecting data from the founder organisms in the phenotron indicative of a parameter of the health of the one or more test founder organisms compared to the one or more control founder organisms, where the data is collected without sensors; and determining from the data whether the exposure condition has an adverse effect on the health of the one or more test founder organisms.

The phenotron assay can include inputting the data into a computing system, so that the computing system can mathematically analyze the data for health information. Also, the computing system can manipulate the data for generating a visual indicator, such as a graph, chart, or the like that illustrates the determination of the adverse effect on health.

The phenotron assay can also include identifying a biological network associated with an aspect of health adversely affected by the exposure condition. When a biological network is identified, the biological pathways thereof can be investigated for being associated with the aspect of health adversely affected by the exposure condition. It can be advantageous to identify a biological component of the biological pathway that is affected by the exposure condition. In order to perform molecular biology or mechanistic studies, one or more biological components of the biological pathway can be selected for further analysis. This can allow for the effect of the exposure condition on the one or more biological components of the biological pathway to be performed in order to determine the biological function of the one or more biological components in response to the exposure condition.

In one embodiment, the phenotron can be conducted for various periods of time depending on the organism as well as the exposure condition being studied. As such, data collecting can be performed for a desired period of time. For example, the data collecting can be at least 1 week, 1 month, 3 months, 6 months, 9 months, or 1 year. Longer studies could be performed if desired or needed.

In one embodiment, the exposure condition is a substance. The substance can include a natural and/or unnatural substance. An unnatural substance can be present in the environment, food, consumer product, article of manufacture, process of manufacture, house product, therapeutic, dietary supplement, or the like. Examples can be chemicals, nutraceuticals, drugs, pesticides, food ingredients, cosmetics, preservatives, additives, chemical components of products (e.g., food containers or utensils) or in the production thereof, components of compositions for internal use, components of compositions for external use, or the like. Specific examples can include heavy metals, lead, cadmium, arsenic, plasticizers, bisphenol, herbicides, atrazine, and others. There are an estimated 100,000 human-made or human-introduced substances now in the environment that were not present in prehistoric times.

There are many other organism insults beyond environmental toxins that are in desperate need of sensitive methods for detecting health and vigor declines. These insults include: air and water pollutants, allergens, immunogens, vaccines, therapeutic agents, pathogens, electromagnetic radiation, excess or deficiencies of nutrients, food additives, genetic manipulations, to name a few. Determining the significance of such insults on health and vigor will have major impacts on medicine, conservation biology and environmental protection and health-risk evaluation.

In one embodiment, the exposure is a condition. The condition can include a natural and/or unnatural environmental condition. Natural environmental conditions can include sunlight, light or darkness exposure lengths, plants, animals, microbes, mating patterns, air components, particulates, altitude, humidity, or the like. Unnatural environmental conditions can include radiation, electromagnetic radiation, X-rays, mobile phone radiation, RFID emissions, pollutants, industrial waste, radioactive emissions, fertilizers, contaminated water, or the like. The examples are nearly infinite.

In one embodiment, the organism can be a multi-cellular organism. The organisms can be mammals, fish, birds, reptiles, arachnids, insects, mollusks, nematodes, or the like. Specific examples can be dogs, cats, rats, mice, primates, *Drosophila*, or the like. In one embodiment, the organism can be unicellular, such as bacteria.

In one embodiment, the control founder organisms are sham exposed. A sham exposure can be configured to mimic the exposure of the test founder organisms; however, the exposure being tested on the test founder organisms is not supplied. For example, a sham exposure of a substance would be administering a composition that does not have the substance, such as a water or carrier composition devoid of a drug or chemical.

In one embodiment, the founder organisms are of equal male and female populations. However, the founder populations can be weighted to be more male or more female depending on the study. In some instance, a single male organism may dominate and control a higher number of female organisms, which may result in the population having more female organisms. On the other hand, the same scenario can include comparatively more male organisms so as to increase the competition for females.

In one embodiment, the number of test founder organisms is the same as the control founder organisms. The use of equal numbers of test and control founders allows for the health effects to be more accurately monitored. However, in some instances it may be advantageous to use a higher number of test or control founders because it may provide data that shows the level of competitive handicap experienced by the test mice or control mice. The test founders can be all male, all female or both, as with the control founders. In some instance only male founders are test or control founders.

In one embodiment, the phenotron includes a cage system that encloses the founders and prevents escape into the environment. The cage system can be configured for indoor or outdoor use. Outdoor phenotrons can be above ground, both above and below ground, or below ground. The indoor phenotrons typically include above-floor cage systems. Standard cage, fence, or other enclosure materials can be used.

In one embodiment, the phenotron is divided into two or more distinct regions. Each region can have one or more feeding stations. Each region can have one or more nesting areas, such as nesting boxes. Also, the distinct regions can be parsed into favorable feeding box regions, unfavorable feeding box regions, favorable nesting areas, unfavorable nesting areas, or the like. The distinct regions can all be substantially similar in size or can vary drastically in size and be configured into favorable or unfavorable regions.

In one embodiment, the test founder organisms are exposed to the exposure condition at conception, gestation, birth, early development, prepubescent development, postpubescent development, continuously, intermittently, or the like. The exposure can be administered at set intervals, randomly, during feeding and/or drinking, during the day and/or night, at a set time daily, or the like.

In one embodiment, the phenotron includes one or more feeders having or being associated with one or more sensors. The feeders having sensors can be used to acquire data regarding the test and control founders. Also, the sensors can be configured to provide test food to test founders when sensing a test tag, and can be configured to provide control food to control founders when sensing a control tag. Additionally, the phenotron can include test feeders that only provide food to test founders upon sensing a test tag, and include control feeders that only provide food to control founders upon sensing a control tag. Alternatively, the test and control feeders can be retained within separate test and control feeding areas that can only be accessed by test or control founders having the appropriate tag. A similar concept of controlled access using the test and control tags with sensors can be applied to watering areas, test areas, control areas, and the like.

In one embodiment, the assay can include tagging the progeny of test founder organisms with test tags, and tagging the progeny of control founder organisms with control tags. Alternatively, the progeny can be maintained in the phenotron sans tags.

In one embodiment, the assay can include removing test and control progeny from the phenotron at one or more select time points. The removal of progeny can be conducted at various stages of development post-birth depending on the goals of the study. For example, the progeny can be removed at birth, at or after weaning, pre-pubescence, post-pubescence, or at fixed intervals, such as when the progeny reach 5 weeks before they mature.

In one embodiment, the assay can include identifying the parentage of progeny of test and/or founder progeny. The parentage can be assessed by various techniques, such as by testing the blood type, genetics, or the like. In some instance visual determination can be used for assessing parentage.

In one embodiment, the tags are passive integrated transceiver (PIT) tags. However, the tags can be any type of tag that emits a signal. The tags can be transmitters or transceivers. It may be possible to use RFID tags, or any other tag that can be utilized as described herein. Also, the tags can include microchip components capable of receiving, storing, and transmitting various types of data. In advanced systems, biometric-capable microchips may be employed so that various types of biometric data can be obtained. The tags can operate on the same frequency or wavelength, or the like. Also, each tag can be unique compared to other tags. The tags can also be configured to provide data to the sensors when two or more tags come into a specified proximity. This can include test-test, test-control, and control-control tag proximities. Further, the tags can be configured with the sensor to provide the location of a tag with respect to the phenotron and other tags during the study. This can be used to map the activity of the founders having the tags.

In one embodiment, the test founders are genetically distinguishable from the control founders. For example, the test and control founders can be selected based on genetic identity so that the members of the test founders can be genetically distinguished from the control founders, which allows for the test and control progeny to be distinguished. The test and control founders can have distinguishable Y chromosome markers and/or mitochondria marchers, such that the markers do not overlap between the test and control founders. This can also allow for analysis of progeny that have a test or control father with the opposite type of mother, and vice versa.

In one embodiment, only male or female founders are test and control founders.

In one embodiment, the assay can include introducing one or more null founders (e.g. male and/or female), said null founders being neither test nor control founders.

In one embodiment, the trans-generational effects of the exposure condition can be analyzed. The trans-generational effects can be associated to exposures to the mother or father that have consequences in the progeny. For example, a toxin induced phenotypic change can occur within an exposed mother and be passed to the progeny in a stable, and heritable way. Thus, trans-generational effects can be studied across two or more generations.

In one embodiment, the assay can include visual analysis of the test and control founders. Visual analysis can be conducted live, via video recording, or the like. As such, discussions of sensors herein can include video recorders as sensors. A person can visually monitor various indicators of health or lack thereof and then record the observations for analysis. Alternatively, the phenotron can include one or more video recorders and/or audio recorders to record various indicators of health, which can be reviewed thereafter. The visual analysis data can be combined with the sensor data in order to assess the health of the founders or the consequences of the exposure condition.

In one embodiment, the data acquired from the phenotron can be related to one or more of: social status, aggressive behavior, outcomes of aggressive behavior, territories, territory foundation, territory maintenance, territorial changes, territorial boundaries, territorial size, female settlement populations or populations, female settlement numbers, female settlement patterns, male to female ratios in territories, pregnancies, liter size at birth, liter size at defined time periods, liter size at weaning, health characteristics of progeny, mating encounters, age of survival, sex-based survival times, test or control-based survival times, fertilities, size, weight, coat condition, or combinations thereof. However, various other types of data related to overall health or health in a specific area can be obtained.

In one embodiment, the one or more sensors can receive data on a continual basis. As such, full time monitoring can be conducted, and the sensors can provide the data to the computing system for storage and analysis.

In one embodiment, the invention can be a phenotron system as described herein. A phenotron can include one or more of the following: an enclosure configured to retain one or more organisms of the same type; one or more distinct regions of the enclosure; one or more feeders within each region; one or more nesting areas within each region; one or more sensors or video recorders configured to be operably associated with each one or more feeders and/or one or more nesting areas; one or more transmitting devices configured to be operably associated with the one or more sensors; a computing system configured for communicating with the one or more transmitting devices to receive data from the one or more sensors; a receiver configured to be operably coupled with the computing system so as to be capable of communicating with the one or more transmitting devices; one or more tags configured to be associated with one or more organisms and for communicating with the one or more sensors, wherein the one or more tags can be configured for communicating data to the one or more sensors. The enclosure can include a cage system that encloses the one or more organisms and prevents escape into the environment outside of the cage system. The cage system can include an openable closure element for access into the cage system, said openable closure element being operable by a human. Also, the cage system can be configured for indoor or outdoor use. For example, the outdoor cage system can be configured be above ground and/or below ground. The cage system can be configured to retain one of mammals, fish, birds, reptiles, arachnids, insects, mollusks, nematodes, bacteria, fungi, or *drosophila*. For example, the cage system can be configured to retain one of dogs, cats, rats, mice, primates, fish, bacteria, fungi, or *drosophila*.

In one example, a phenotron is created by providing a large dark plastic bin in four of six subdivisions of the phenotron. Each of which contain four nesting boxes and a food supply. It is thought that the mice perceive these subdivisions as optimal because the bins are dark and have mouse size entrances. Thus, they are perceived to be predator free. Invariably they are territories owned by a single male and a few females. Most of the observed contests (fights) among males are over these optimal territories (habitats). The two suboptimal habitats have no dark, "predator-free" structures. Usually one male owns one of these suboptimal territories with a few females and the all the other animals are forced into the final suboptimal territory which is undefended. The fitness (reproductive success) of animals in this undefended suboptimal territory is considerably lower than animals settled in the defended territories.

The phenotrons can be automated with sensors, transmitters, a network, receivers, and a central computing system. Also, standard network equipment such as routers, servers, data lines, wireless components, and the like can be included. The automation allows for data collection by the acquisition of PIT (passive integrated transceiver [RFID]) tags and PIT tag readers (Biomark, Boise, Id.). PIT tags are implanted in every individual and PIT tag readers are set at each feeder in a population allowing continuous transmission of feeder visitation information over a wireless network to a dedicated computer. Each feeder is associated with a set of nest boxes in either one of four optimal territories (nest boxes in enclosed structures) or two suboptimal territories (nest boxes in open). This design identifies dominant territorial males and subsequent changes in social dominance and female settlement patterns.

For example, we have conducted 10 populations with this new data collection design and invariably 5 feeders are defended by a single male and a small group of females and the remaining males and females are forced to feed at 1 suboptimal, undefended feeder. The reproductive output per male for single-male defended territories are 3 times higher than in multi-male undefended territories ($p<0.0001$) and the similar comparison for females shows an almost two-fold difference in reproductive output ($p<0.01$). These data reveal considerable variation in male and female fitness allowing the detection of differential components of fitness for treatment and control mice.

Normally, we initially conduct 6 populations for each treatment. Each population will run anywhere from 1 to 8 months depending on the strength of the effect and the nature of the physiological defect created by the treatment. So for example if the only defect is the ability of males to gain territories, then we obtain this information in the first month. However, if other defects are caused, it often takes additional months for the defects to reveal themselves.

We have also demonstrated that enclosures consisting of 30 cages on five shelves interconnected by tubing (e.g. plaster, wood, metal, etc.) to create optimal habitats (dark and easy to defend) and suboptimal habitats (exposed to light and less easy to defend) produce social outcomes similar to our traditional enclosures. Such modifications will allow more efficient use of space for commercial applications.

Toxin administration can take many forms depending on how the suspected toxin is expected to be exposed to humans. Thus almost any exposure route present in humans can be emulated in mice. For example, dermal exposure can be emulated by applying the substance to skin of mice.

Exposure of mice to HFCS has been done through dietary exposure. For such chronic dietary (or water) exposure we envision exposing mother and father for selected time periods prior to conception of the animals to be tested and during gestation and nursing. This maximizes the opportunity of detecting a health effect. When the pups are weaned they are provided the experimental food up to the time they are to be released into the seminatural enclosures (phenotrons). This protocol maximizes the opportunity for the tested substance to cause health declines because the animals are exposed during the sensitive developmental periods prior to adulthood. The control animals are treated identically, except they are sham-exposed to the treatment. Gestation is 3 weeks and offspring are weaned 6 weeks after conception or 3 weeks after birth. Weaned offspring will continue to be exposed until they are 8-12 months of age at which point they will either enter populations, become colony-housed controls or be utilized for other experimental measures. Controls will be age matched and undergo identical environmental and exposure conditions except they are sham-exposed to the suspected toxin.

Also, exposure can be facilitated by a system that will only allow specified animals according to their pit tag numbers to visit specific water or feeding locations within the seminatural enclosures. This will allow specific treatments to continue in the seminatural populations without the test exposure condition being subjected to the controls.

EXPERIMENTAL

Experimental data is provided as evidence of the ability of the phenotron assay in detecting adverse health consequences. It is reported that fitness studies conducted in phenotron assays showed adverse health consequences for one potential toxin and genetic treatments, previously thought to have no adverse effects. The phenotrons demonstrate large fitness consequences associated with each treatment, confirming the power and sensitivity of social competition to reveal health and performance differences that are difficult to detect under benign laboratory conditions. Furthermore, fitness differences are not artificially amplified; they are conservative estimates of the differential reproductive success that would occur in nature. Thus, these measures provide the fitness defect caused by the treatment, and also indicate that there are underlying molecular and physiological defects to be discovered.

EXAMPLE 1

Figure 2:
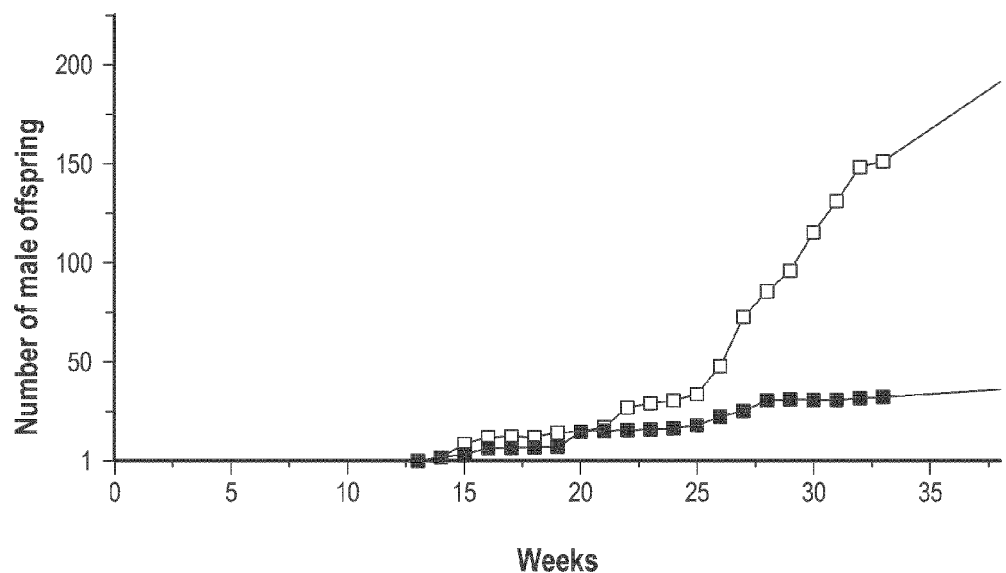
FIG. 2 is a graph that illustrates the relative reproductive success of inbred and outbred males in a phenotron.

Full-sib inbreeding is shown to be 50 times worse than reported by previous studies. The primary cause of inbreeding depression is the expression of deleterious recessive alleles that are expressed at a higher rate in inbred individuals. These negative consequences have been well established for centuries. Two major studies have been conducted on mice and the reproductive consequences of one generation of full-sib matings were estimated at about a 10% decline; most of the effect was due to reduced litter size (an effect we also found). Since the surviving offspring all seemed healthy the previous studies stopped their investigation. However, we conducted phenotron assays on these seemingly normal inbred progeny by competing them against outbred controls and discovered an additional 500% fitness decline (FIG. 2). Outbred males had five times more offspring than inbred males—a 50-fold increase over previous studies. Inbred females also suffered significant fitness declines, though they were smaller than those for males.

Figure 3:
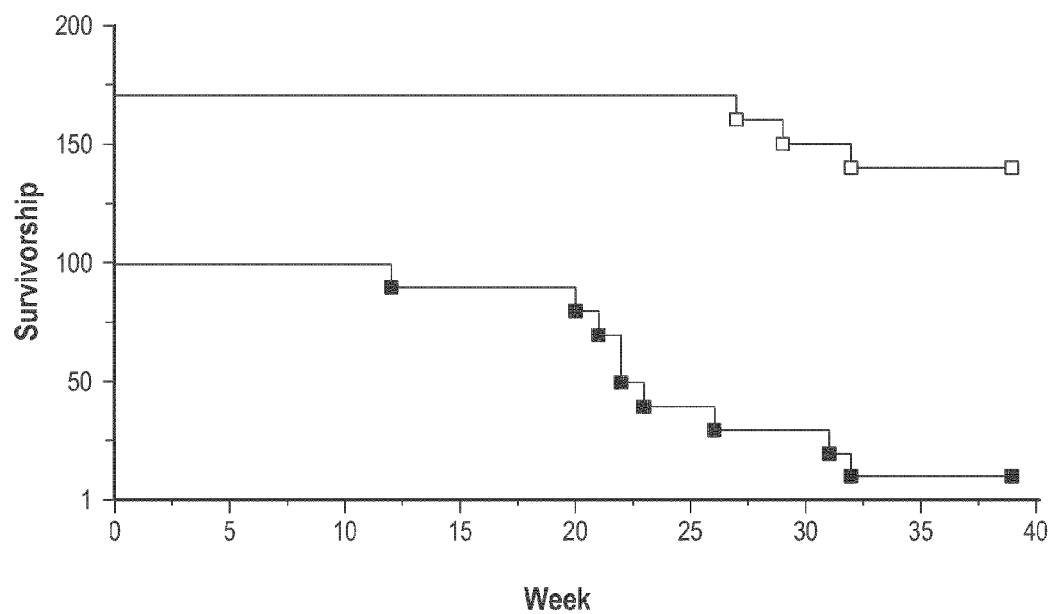
FIG. 3 is a graph that illustrates the relative survivorship of inbred and outbred males in a phenotron.

The dramatic fitness declines in inbred males were primarily attributable to a 41% reduced ability to gain territories (p=0.04) and decreased survival (p=0.001), which was particularly true for territorial inbred males where 90% had died by the end of the experiment as compared to only 24% of outbred territorial males (FIG. 3; p=0.0001). This suggests that inbred males had difficulty both acquiring and maintaining territories and that our results are conservative, as reflected in the differences in slopes of their reproductive output at 40 weeks (FIG. 2), which only represents ½ to ⅔ of the mouse lifespan. We maintained sibs of outbred and inbred founders in the colony and they showed no differences in survival or reproductive output, highlighting the tremendous environment-dependent phenotypic differences missed by previous studies.

We have repeated these experiments with inbreeding at the level of cousin unions, which should reduce the proportion of deleterious recessive genes expressed by ¾. In phenotron assays, first cousin-level inbreeding reduced male fitness by 34% in non-infected populations (p<0.001) and by 57% in *Salmonella* infected populations (p<0.001). Under benign laboratory conditions cousin-level inbreeding had no influence on reproductive output, survival or *Salmonella* clearance, which again shows the sensitivity of phenotron assays for revealing large fitness declines that were invisible in the laboratory.

EXAMPLE 2

It has now been found that the four-decade-old paradox of the t-complex can be solved by phenotron assays. Since its discovery half a century ago, the mouse t complex has become a textbook example of a selfish gene. Despite much success characterizing its underlying genetics and transmission distortion effects, the population dynamics of this persistent genetic polymorphism has remained paradoxical because population frequencies are far lower than theoretical predictions would suggest. The t-bearing males are characterized by a meiotic drive phenotype. Although a heterozygote male produces t and + sperm in equal proportions, t sperm sabotage+sperm causing flagellar dysfunction, resulting in greater than 90% of his offspring inheriting a t haplotype. In contrast, females transmit t-bearing gametes in Mendelian ratios. Based on the extreme t-biased transmission found among male gametes (and correcting for t homozygous lethality/male sterility), over 70% of wild mice should be t carriers, but the frequencies of t bearing mice are far lower, averaging 6-25%. Thus, it is likely that some form of selection is operating against the invasion and spread of t haplotypes among wild mouse populations.

Figure 4:
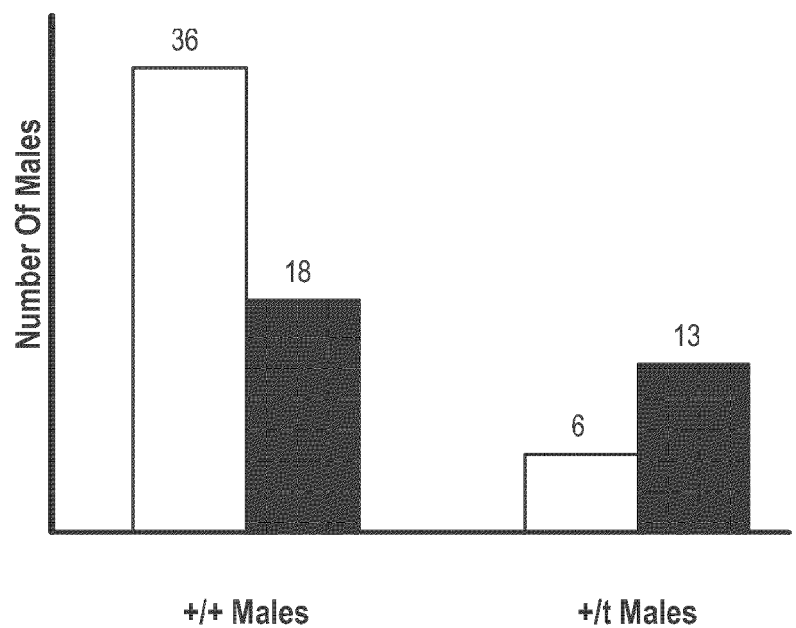
FIG. 4 is a graph that illustrates a comparison of dominant and subordinate status of males in a phenotron.

We have used our phenotron approach to discover the missing phenotypes associated with the t complex, thereby solving this four-decade-old paradox. We demonstrated that fitness declines in t bearing males and females reduced t allele frequencies to 49% below transmission distortion expectations (p=0.005) and 34% below Mendelian expectations (p=0.04). The overall decline of t allelic frequency was primarily due to two fitness components. First, +/+ males were twice as likely to become dominant as subordinate, whereas +/t males were twice as likely to be subordinate (FIG. 4; p<0.02). This was the proximate cause of +/+ males producing twice as many progeny as +/t males on average. Second, +/+ females produced 50% more progeny than +/t females. Part of this effect was due to a significantly reduced survival of +/t females (p<0.03). These data collectively suggest that selection against t-bearing heterozygotes in natural populations can easily resolve the paradox of why t frequencies in nature are so low.

These results demonstrate that genetic variants with observable lab phenotypes can have additional important phenotypes whose expression is largely invisible using conventional assays. The phenotron assay of t-bearing mice revealed important fitness declines in males and females that had gone undetected for 40 years and dozens of laboratory studies. Similarly, toxins often impact multiple physiological systems, so even if toxicity is known for a particular toxin, phenotron assays can reveal critical, but otherwise hidden, defects.

EXAMPLE 3

A phenotron assay has now revealed new functions for histocompatibility (MHC) genes. There are numerous examples of toxins having unexpected adverse effects given the current understanding of how they might impact physiological systems. Since phenotron assays screen most physiological and behavioral systems, they provide a broad screen for unanticipated results. For example, we discovered two major behavioral functions of histocompatibility genes when we were expecting to find disease phenotypes caused by infectious agents.

The phenotron showed MHC-mediated sexual selection. We conducted phenotron assays designed to determine whether MHC heterozygotes were more fit than homozygous conspecifics, due to hypothesized superior immunocompetence. We discovered a deficiency of MHC homozygous offspring in all populations, with a mean deficiency of 27%. This was consistent with the homozygote disadvantage hypothesis, but we were able to show that MHC homozygotes were missing not because they were falling victim to disease, but because females preferred to mate with MHC dissimilar males. Behavioral observations and genetic parentage analysis indicated that females were the protagonists of the study, leaving their territories to engage in extra-pair matings preferentially with males whose MHC genotype was dissimilar to their own. Testing mice in the context of Mus phenotron populations demonstrated that the selection coefficient arising from non-random mating was strong enough to maintain the allelic diversity found in surveys of wild populations, suggesting that mating preferences could indeed be the elusive source of selection maintaining MHC polymorphisms.

This and similar studies prompted the search for the molecular and physiological basis for how MHC-mediated odors are detected. Recently, it was demonstrated that mice have olfactory sensory neurons expressing receptors that bind peptides in an MHC-like fashion. This discovery seamlessly links selection acting either on MHC-mediated behaviors or immune recognition because both forms of selection ultimately act on the peptide binding properties of MHC molecules. This discovery provides the molecular logic behind MHC-mediated mating preferences observed in humans and many vertebrates. The central theme is that histocompatibility genes are so important for disease resistance that special reproductive mechanisms have evolved to produce offspring more resistant to both infectious and genetic disease. This is an example of how phenotron assays contribute to the identification of molecular and physiological bases of phenotypes.

EXAMPLE 4

Figure 5:
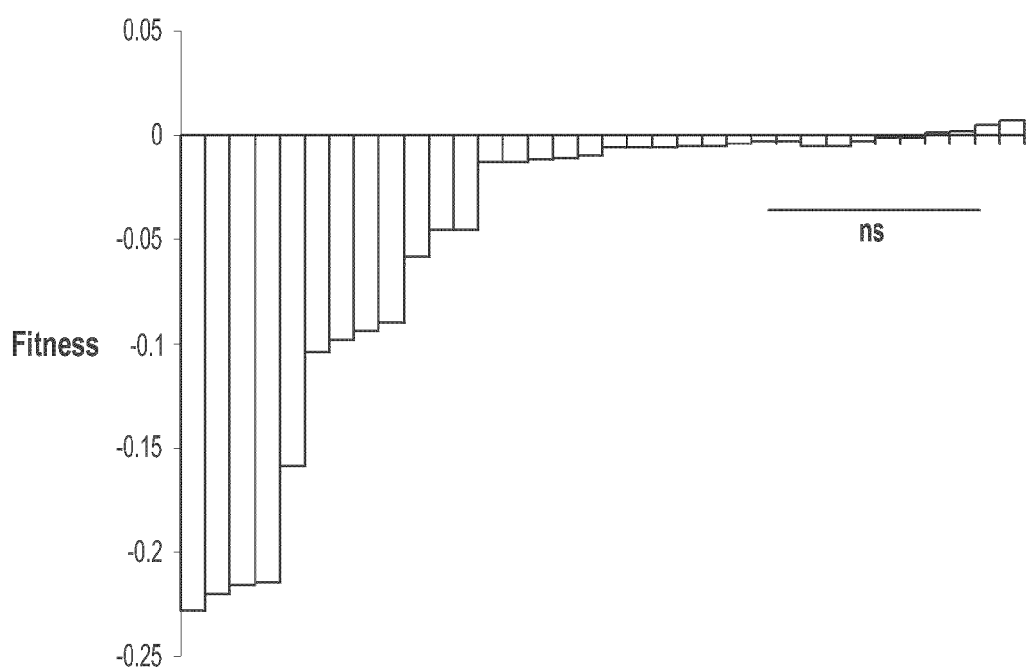
FIG. 5 is a graph that illustrates the fitness distribution of yeast knockout mutants compared to wild type in a phenotron.

Phenotrons have proven powerful in non-mammalian systems revealing phenotypes in *Saccharomyces* and *Drosophila*. Many yeast knockout mutants express no detectable phenotype when grown in culture without competition. FIG. 5 shows the fitness distribution of 34 of these knockouts subjected to direct competition with wild type. Approximately ⅓ maintained their no-phenotype status, but ⅔ expressed significant fitness declines ranging from 0.5% to 22%; two knockouts showed a significant fitness increase compared to wild type. By analogy, competition became a microscope that made the formerly invisible phenotypes visible.

Similar results have been demonstrated in *Drosophila*. Mutations were allowed to accumulate in populations of *Drosophila* for 30 generations. These mutation accumulation lines were competed against wild type to test for fitness declines either under benign or harsh competitive conditions. The fitness declines under harsh population conditions (limited food) were approximately 60% (2% per generation). However, the final fitness decline under benign population conditions was only 5%, an order of magnitude lower than under harsh conditions. Similar competition-amplified fitness effects have been demonstrated for inbreeding in *Drosophila*.

EXAMPLE 5

Phenotron assays have shown that the consumption of dietary fructose causes dramatic fitness declines. Fructose consumption specifically in the forms of sucrose and high fructose corn syrup (HFCS) have been at the center of debate concerning the obesity epidemic and associated disease states. Recent increases in obesity correlate with both increased total fructose consumption and increased intake of free fructose (HFCS), though the later correlation is stronger.

Two phenotron assays were conducted to capture negative performance consequences of fructose diets: the first competition was between animals reared on diets containing a 1:1 ratio of fructose and glucose monosaccharides (approximating HFCS) and mice fed sucrose; the second competition was between animals on the fructose/glucose diet and starch fed individuals. All three diets were identical except for a portion of their carbohydrate composition, with 25% of calories coming from fructose/glucose, sucrose or starch.

Figure 6A:
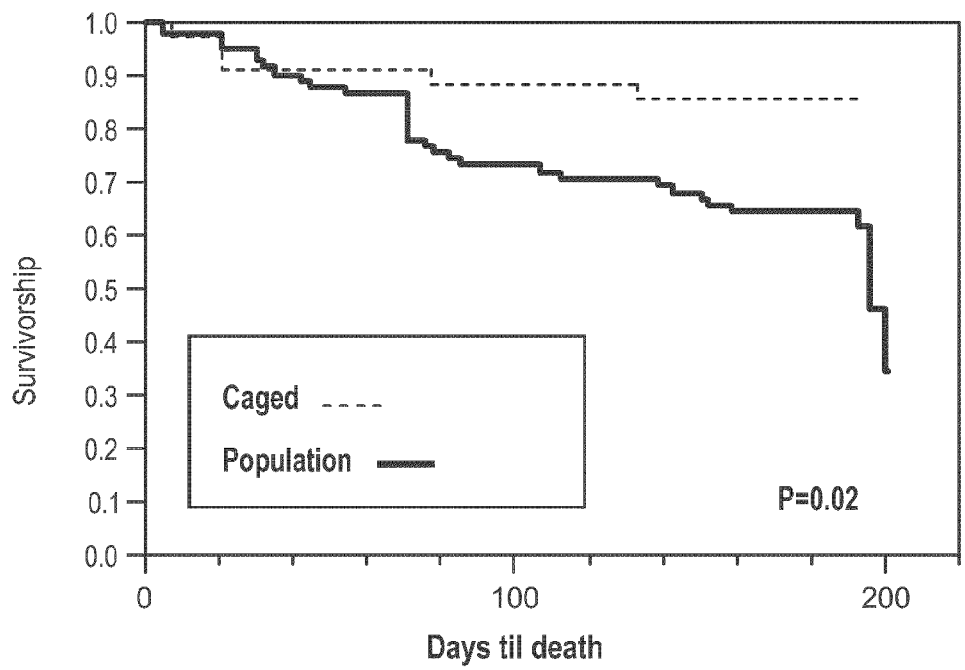
FIG. 6A is a graph that illustrates the differential survival between caged and phenotron mice having a high fructose corn syrup diet.

Population founders were exposed to diets that differed only in carbohydrate composition, with 25% of daily kcal coming from either HFCS or sucrose. An exposure level of 25% simple sugar (12.5% fructose) was selected because this is the upper recommended intake limit established by the FDA for added sweetener and because this dose is experienced by 20% of Americans. Exposure began at weaning (3-4 weeks of age) and continued for 6 months, at which point animals entered the phenotron. Phenotron assays ran for 200 days, spanning over one-half to three-quarters of the average mouse lifespan. It is important to note that over this same period a subset of exposed individuals from each dietary treatment group remained in cages to provide caged comparisons for weight and mortality data. The intense stresses associated with mouse social ecology in the phenotron can be visualized by comparing the differential survivorship of individuals within seminatural enclosures and those in remaining in caged environments (FIG. 6A).

Figure 6B:
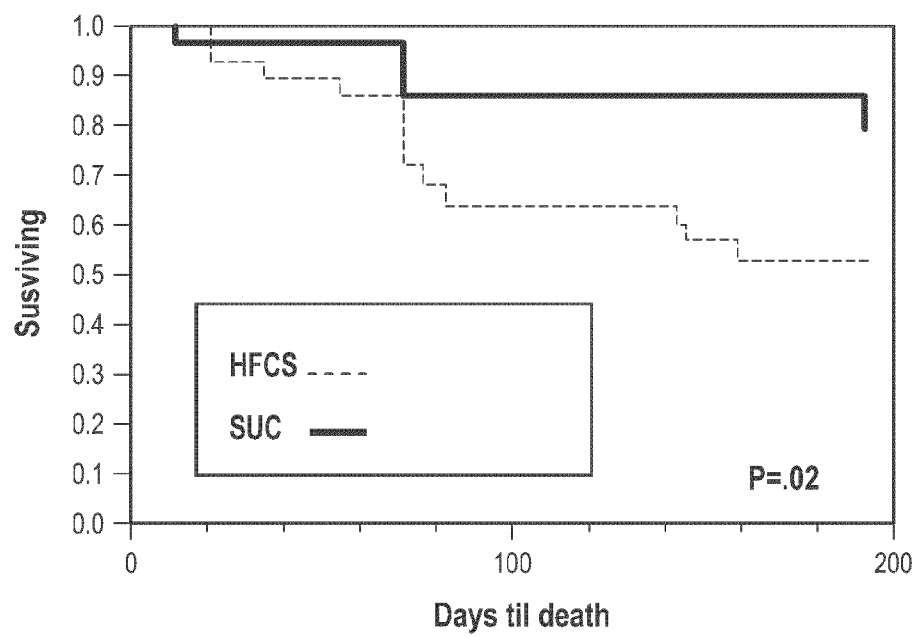
FIG. 6B is a graph that illustrates the differential survival of high fructose corn syrup fed mice compared to sucrose fed mice.

Utilizing phenotron assays we obtained the first direct experimental evidence that the ingestion of HFCS has negative health impacts compared to an equivalent caloric intake of sucrose. During the fructose/glucose versus sucrose comparison female mice raised on the fructose/glucose diet experienced 30% higher mortality than their sucrose-fed counterparts (FIG. 6B, p=0.02). The fructose/glucose versus starch assessment revealed even more dramatic results. Female mortality followed the same pattern observed in the sucrose comparison (p=0.04), with fructose/glucose-fed females experiencing approximately 30% increased mortality within the seminatural enclosures. In addition, a male territoriality effect was observed, where 75% of available territories were controlled by males raised on starch (p=0.03). These robust results demonstrated the adverse effects of the HFCS diet with FDA-sanctioned levels, and thus provide convincing evidence that this in vivo assay provides sensitivity unequalled by other models.

These results demonstrate the sensitivity of phenotron assay in the realm of environmental exposure and provide the framework to apply this approach for testing any suspected toxin or other treatment the may cause degradation in health. With only three populations (we normally conduct six populations) we have significant mortality and territoriality results that are now the lowest observed adverse effect level (LOAEL) of fructose toxicity and the only experimental study indicating differential organism health consequences due to the consumption of fructose and glucose monosaccharides compared to sucrose.

EXAMPLE 6

A phenotron assay has shown that here are no observable fitness consequences of the 'functionally equivalent' $Hoxa3^{D3}$ translocation. Hox genes are a family of transcription factors that regulate early development. They are highly conserved across animal taxa, particularly in relation to their genomic organization. Most vertebrates possess four Hox clusters arising from two ancient genome duplication events. In most species, each of these four Hox clusters have remained together and the linear gene order is preserved, even in taxa as distantly related as *Drosophila*. This conservation of colinearity appears to be important for proper order of gene activation. Targeted disruption of Hox genes usually results in developmental defects.

TABLE 2

Genotypic frequencies for $Hoxa3^{D3}$ ($a3^{D3}$) and wild type (+).

| | Genotypic Frequencies | | |
| --- | --- | --- | --- |
| | $a3^{D3}/a3^{D3}$ | $a3^{D3}/+$ | +/+ |
| Observed | 528 | 778 | 856 |
| Expected | 856 | 1712 | 856 |
| % deficiency | 38% | 55% | — |
| $\chi^2$ probability* | | p < 0.0001 | |

Hoxa3 and Hoxd3 are paralogous genes, located on separate chromosomes and sharing only 50% amino acid sequence identity. They have identical expression profiles, but when these genes are disrupted they have non-overlapping phenotypes, with Hoxa3 showing pharyngeal defects and Hoxd3 showing axial skeletal defects. During reciprocal translocation experiments, it has been showed that Hoxa3 and Hoxd3 completely complemented each other, which was interpreted as functional equivalency. We are currently testing the $Hoxa3^{D3}$ translocation in phenotron populations. We have genotyped 2162 progeny and large, significant fitness declines have emerged. The genotypic frequencies are provided in Table 2. We have assumed the wild type genotype (+/+) has a fitness of 1 and used this to calculate the expected Mendelian frequencies. There is a 38% deficiency of $Hoxa3^{D3}$ homozygotes and a 55% deficiency of $Hoxa3^{D3}$/+ heterozygotes relative to observed +/+ frequencies (p<0.0001). It is difficult to predict what fitness components are causing these fitness declines without doing parentage studies. However, our analysis of male territoriality suggests that this will be a strong component. Only 11% of $Hoxa3^{D3}$ homozygous males have gained territories, whereas 75% of wild type males have gained territories (p=0.005). Male territoriality is a strong predictor of male mating success. Thus, this $Hoxa3^{D3}$ translocation that has no discernible phenotype in the lab, is showing a dramatic fitness defect in semi-natural populations.

We have conducted similar studies on two additional Hox translocations—$Hoxa1^{B1}$ and $Hoxb1^{A1}$. We found no fitness defects associated with these translocations (data not shown). These negative results underscore the other function of phenotron assays for suspected toxins—when mice exposed to a potential toxin show no performance declines in competition with control mice, it becomes evidence supporting the hypothesis that this substance at this dose is safe.

EXAMPLE 7

In one example, phenotron data collection was performed with a plurality of sensors (e.g., PIT readers) configured to acquire information from PIT tags. The PIT tags were implanted in every test and control founder and PIT readers were set at each feeder thereby allowing continuous transmission of feeder visitation information over a wireless network to a dedicated computer, however, the network could be hardwired. Each feeder was associated with a set of nest boxes in either one through four optimal territories (e.g., nest boxes in enclosed structures) or two suboptimal territories (e.g., nest boxes in open without any enclosure). This design identified dominant territorial males, and subsequent changes in social dominance and female settlement patterns. It was conducted that this data collection system was capable of recording important health parameters. There were some feeders being defended by a single male and a small group of females, and the remaining males and females were forced to feed at a single suboptimal, undefended feeder. The reproductive output per male for single-male defended territories was 3 times higher than in multi-male undefended territories (p<0.0001), and the similar comparison for females shows an almost two-fold difference in reproductive output (p<0.01). These data reveal considerable variation in male and female fitness allowing the detection of differential components of fitness for treatment and control mice.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. All references recited herein are incorporated herein by specific reference.

The invention claimed is:
1. A method for determining a consequence of an exposure to an exposure condition, the method comprising:
   identifying an exposure condition to be studied for its effect on an organism, wherein the exposure condition is selected from the group consisting of a potential or known toxin, an environmental stressor, a genetic condition, and combinations thereof;
   providing a phenotron system that includes:
      an enclosure configured for retaining and observing at least one test organism and at least one control organ- ism, wherein the test and control organisms live in the same enclosure and in direct competition with one another;
one or more distinct regions of the enclosure, the distinct regions including one or more feeders and one or more nesting areas; and
sensors associated with the test and control organisms and with the enclosure,
wherein the sensors are configured to control access to the one or more distinct regions of the enclosure and/or to collect information about the test and control organisms related to at least one of physical fitness or at least one social status marker;
introducing at least one test organism and at least one control organism of the same species into the phenotron system, wherein the test and control organisms each have a signal emitting tag that is sensed by the sensors, wherein the at least one test organism is exposed to the exposure condition in the enclosure and, in the same enclosure, the at least one control organism is not exposed to the exposure condition;
collecting, from the one or more sensors, data indicative of a parameter of the physical fitness and/or social status of the at least one test organism as compared to the at least one control organism; and
determining from the data whether the exposure condition has an adverse impact on the physical fitness and/or social status of the at least one test organism.

2. A method as in claim 1, wherein the collecting of data is performed for a desired period of time.

3. A method as in claim 2, wherein the collecting is at least 1 week.

4. A method as in claim 1, wherein the exposure condition is a substance.

5. A method as in claim 1, wherein the exposure condition is an environmental condition.

6. A method as in claim 1, wherein the organism is a multi-cellular organism or single cell organism.

7. A method as in claim 1, wherein the control organisms are sham exposed.

8. A method as in claim 1, wherein the test and control organisms are of equal male and female populations.

9. A method as in claim 1, wherein the number of test organisms is the same as the control organisms.

10. A method as in claim 1, wherein the phenotron includes a cage system that encloses the test and control organisms and prevents escape into the environment.

11. A method as in claim 1, wherein the phenotron is divided into two or more distinct regions.

12. A method as in claim 1, wherein the test organisms are exposed to the exposure condition at conception, gestation, birth, early development, prepubescent development, postpubescent development, continuously, intermittently, or combinations thereof.

13. A method as in claim 12, wherein the phenotron includes one or more feeders having one or more sensors being configured to control the exposure condition.

14. A method as in claim 1, further comprising tagging the progeny of test founder organisms with test tags, and tagging the progeny of control organisms with control tags.

15. A method as in claim 14, further comprising removing test and control progeny from the phenotron at one or more select time points.

16. A method as in claim 14, further comprising identifying the parentage of progeny of test and/or founder progeny.

17. A method as in claim 1, wherein the tags are passive integrated transceiver tags.

18. A method as in claim 1, the test organisms are genetically distinguishable from the control organisms.

19. A method as in claim 1, wherein only males are test and control organisms.

20. A method as in claim 1, further comprising introducing one or more null females into the phenotron, said null females being neither test nor control organisms.

21. A method as in claim 1, further comprising studying trans-generational effects of the exposure condition.

22. A method as in claim 1, further comprising visual analysis of the test and control organisms founders.

23. A method as in claim 1, wherein the data is related to one or more of: social status, aggressive behavior, outcomes of aggressive behavior, territories, territory foundation, territory maintenance, territorial changes, territorial boundaries, territorial size, female settlement numbers, female settlement patterns, male to female ratios in territories, pregnancies, liter size at birth, liter size at defined time periods, liter size at weaning, health characteristics of progeny, mating encounters, age of survival, sex-based survival times, test or control-based survival times, fertilities, size, weight, coat condition, or combinations thereof.

24. A method as in claim 1, wherein the sensor receives data on a continual basis.

25. A method as in claim 1, further comprising supplying the data to a computing system.

26. A method as in claim 25, further comprising analyzing the data with the computing system.

27. A method for determining an adverse effect of an exposure to an exposure condition, the method comprising:
identifying an exposure condition to be studied for its effect on an organism, wherein the exposure condition is at least one of inbreeding, genetic abnormalities, a known or suspected toxin selected from the group consisting of pollutants, industrial waste, fertilizers, heavy metals, lead, cadmium, arsenic, plasticizers, bisphenol A, herbicides, atrazine, chemicals, nutraceuticals, drugs, pesticides, food ingredients, cosmetics, preservatives, food additives, chemical components of food container or eating utensil products, air and water pollutants, allergens, immunogens, vaccines, therapeutic agents, pathogens, radiation, electromagnetic radiation, excess or deficiencies of nutrients, plants, animals, particulates, microbes, and combinations thereof, or an environmental condition selected from the group consisting of sunlight, light or darkness exposure lengths, mating patterns, altitude, humidity, X-rays, mobile phone radiation, RFID emissions, contaminated water, and combinations thereof;
introducing one or more test organisms and one or more control organisms of the same species into a phenotron system that includes:
an enclosure configured for retaining and observing at least one test organism and at least one control organism, wherein the test and control organisms live in the same enclosure and in direct competition with one another,
wherein the one or more test organisms are exposed to the exposure condition in the enclosure and, in the same enclosure, the one or more control organisms are not exposed to the exposure condition
one or more distinct regions of the enclosure, the distinct regions including one or more feeders and one or more nesting areas; and
sensors associated with each of the test and control organisms and associated with the enclosure, wherein the sensors are configured to control access to the one or more distinct regions of the enclosure and/or to collect information about the test and control organisms related to at least one of physical fitness or at least one social status marker;

collecting data from the test and control organisms in the phenotron data indicative of a parameter of the physical fitness and/or social status of the one or more test organisms as compared to the one or more control organisms; and determining from the data whether the exposure condition has an adverse impact on the physical fitness and/or social status of the one or more test organisms.

28. A method as in claim 27, further comprising inputting the data into a computing system.

29. A method as in claim 28, further comprising mathematically analyzing the data with the computing system.

30. A method as in claim 29, further comprising generating a visual indicator that illustrates the determination of the adverse effect on health.

31. A method as in claim 27, further comprising identifying a biological network associated with an aspect of health adversely effected by the exposure condition.

32. A method as in claim 31, further comprising identifying a biological pathway of the biological network, said biological pathway being associated with the aspect of health adversely effected by the exposure condition.

33. A method as in claim 32, further comprising identifying a biological component of the biological pathway, said biological component being affected by the exposure condition.

34. A method as in claim 32, further comprising identifying one or more biological components of the biological pathway.

35. A method as in claim 34, further comprising assaying the effect of the exposure condition on the one or more biological components of the biological pathway.

36. A method as in claim 35, further comprising determining the biological function of the one or more biological components in response to the exposure condition.

37. A phenotron system configured for observation of a potential fitness decline in an organism as a result of exposure to an exposure condition selected from the group consisting of a potential or known toxin, an environmental stressor, a genetic condition, and combinations thereof, the phenotron system comprising:

an enclosure configured for retaining and observation of at least one test organism and at least one control organism, wherein the test and control organisms live in the same enclosure and in direct competition with one another, wherein the at least one test organism is exposed to the exposure condition in the enclosure and, in the same enclosure, the at least one control organism is not exposed to the exposure condition, and wherein the test and control organisms are of the same species;

one or more distinct regions of the enclosure, the distinct regions including one or more feeders and one or more nesting areas; and sensors associated with the test and control organisms and with the enclosure, wherein the sensors are configured to control access to the one or more distinct regions of the enclosure and/or to collect information about the test and control organisms related to at least one of fitness or at least one social status marker.

38. A phenotron system as in claim 37, further comprising one or more transmitting devices configured to be operably associated with the one or more sensors.

39. A phenotron system as in claim 38, further comprising a computing system configured for communicating with the one or more transmitting devices to receive data from the one or more sensors.

40. A phenotron system as in claim 39, further comprising a receiver configured to be operably coupled with the computing system so as to be capable of communicating with the one or more transmitting devices.

41. A phenotron system as in claim 37, further comprising one or more tags configured to be associated with one or more organisms and for communicating with the one or more sensors.

42. A phenotron system as in claim 41, wherein the one or more tags are configured for communicating data to the one or more sensors.

43. A phenotron system as in claim 37, wherein the enclosure includes a cage system that encloses the one or more organisms and prevents escape into the environment outside of the cage system.

44. A phenotron system as in claim 43, wherein the cage system includes an openable closure element for access into the cage system, said openable closure element being operable by a human.

45. A phenotron system as in claim 44, wherein the cage system is configured for indoor or outdoor use.

46. A phenotron system as in claim 45, wherein the outdoor cage system is configured be above ground and/or below ground.

47. A phenotron system as in claim 44, wherein the cage system is configured to retain one of mammals, fish, birds, reptiles, arachnids, insects, mollusks, nematodes, bacteria or *drosophila*.

48. A phenotron system as in claim 47, wherein the cage system is configured to retain one of dogs, cats, rats, mice, primates, or drosophila.

49. A method as in claim 1, wherein the exposure condition is at least one of inbreeding, genetic abnormalities, a known or suspected toxin selected from the group consisting of pollutants, industrial waste, fertilizers, heavy metals, lead, cadmium, arsenic, plasticizers, bisphenol A, herbicides, atrazine, chemicals, nutraceuticals, drugs, pesticides, food ingredients, cosmetics, preservatives, food additives, chemical components of food container or eating utensil products, air and water pollutants, allergens, immunogens, vaccines, therapeutic agents, pathogens, radiation, electromagnetic radiation, excess or deficiencies of nutrients, plants, animals, particulates, microbes, and combinations thereof, or an environmental condition selected from the group consisting of sunlight, light or darkness exposure lengths, mating patterns, altitude, humidity, X-rays, mobile phone radiation, RFID emissions, contaminated water, and combinations thereof.

\* \* \* \* \*

UNITED STATES PATENT AND TRADEMARK OFFICE
CERTIFICATE OF CORRECTION

| | | |
|---|---|---|
| PATENT NO. | : 8,304,208 B2 | Page 1 of 1 |
| APPLICATION NO. | : 12/994394 | |
| DATED | : November 6, 2012 | |
| INVENTOR(S) | : Potts et al. | |

It is certified that error appears in the above-identified patent and that said Letters Patent is hereby corrected as shown below:

In the Specification

Column 1
Line 11, Insert new paragraph with heading --GOVERNMENT LICENSE RIGHTS This invention was made with government support under GM039578 awarded by National Institute of Health. The government has certain rights in the invention.--

Signed and Sealed this
Thirty-first Day of March, 2015

Michelle K. Lee
*Director of the United States Patent and Trademark Office*